United States Patent [19]

Shimasaki et al.

[11] Patent Number: 4,774,218

[45] Date of Patent: Sep. 27, 1988

[54] CATALYST FOR VAPOR-PHASE INTRAMOLECULAR DEHYDRATION REACTION OF ALKANOLAMINES

[75] Inventors: Yuuji Shimasaki, Takatsuki; Hideaki Tuneki, Suita; Youichi Hino, Sakai; Hitoshi Yano, Suita; Michio Ueshima, Takarazuka, all of Japan

[73] Assignee: Nippon Shokubai Kagaku Kogyo Co., Ltd., Tokyo, Japan

[21] Appl. No.: 943,085

[22] Filed: Dec. 18, 1986

[30] Foreign Application Priority Data

Dec. 27, 1985 [JP] Japan .................................. 60-292541
Nov. 11, 1986 [JP] Japan .................................. 61-266585
Nov. 11, 1986 [JP] Japan .................................. 61-266586
Nov. 11, 1986 [JP] Japan .................................. 61-266587

[51] Int. Cl.$^4$ ........................ B01J 27/16; B01J 27/18
[52] U.S. Cl. ................................. 502/202; 502/208; 502/210; 502/211; 502/214; 423/3.5; 548/969
[58] Field of Search ............... 502/202, 208, 214, 210, 502/211; 548/969; 423/305

[56] References Cited

U.S. PATENT DOCUMENTS

| | | | |
|---|---|---|---|
| 4,065,510 | 12/1977 | Schreyer et al. | 502/208 X |
| 4,289,656 | 9/1981 | Hayes et al. | 502/311 |
| 4,363,748 | 12/1982 | Crum et al. | 502/208 |
| 4,495,374 | 1/1985 | Jones et al. | 502/208 X |

Primary Examiner—W. J. Shine
Attorney, Agent, or Firm—Sherman and Shalloway

[57] ABSTRACT

A catalyst for the vapor phase intramolecular dehydration reaction of an alkanolamine represented by the general formula

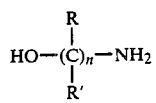
(I)

wherein each of R and R' is selected from hydrogen, a methyl group and an ethyl group, and n is an integer of 2 to 5, to convert it into a cyclic amine represented by the general formula

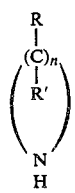
(II)

wherein R, R' and n are as defined above. The catalyst is an oxide composition represented by the following formula

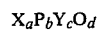

wherein X is at least one element selected from alkali metals and alkaline earth metals, P is phosphorus, Y is at least one element selected from B, Al, Si, S, Sc, Ti, Cu, Y, Zr, Nb, Mo, Sn, Sb, La, Ce, Ta, W, Tl, Pb, Bi and Th, O is oxygen, the suffixes a, b, c and d represent the atomic ratios of the elements X, P, Y and O, and when a=1, b=0.01–3 and c=0–100, and d is a value determined by a, b and c and the state of bonding of the constituent elements.

1 Claim, No Drawings

CATALYST FOR VAPOR-PHASE INTRAMOLECULAR DEHYDRATION REACTION OF ALKANOLAMINES

This invention relates to a catalyst for use in the vapor-phase intramolecular reaction of an alkanolamine of general formula (I) below to convert it into a cyclic amine of general formula (II) below.

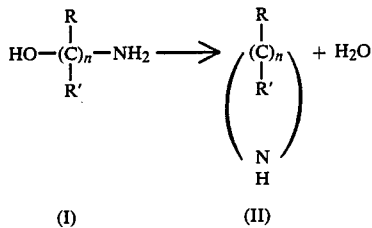

(I)      (II)

In the formulae, R and R' each represent hydrogen, a methyl group or an ethyl group, and n is an integer of 2 to 5.

Generally, cyclic amines of formula (II), particularly aziridine compounds (n=2), have good reactivity and react with compounds having various functional groups. Hence, various derivatives having amino groups can be produced from the cyclic amines. Furthermore, since they can be reacted while retaining rings, derivatives having ring-opening reactivity may be produced from them. Furthermore, polyamine-type polymers can be produced from them by ring-opening polymerization. Accordingly, these cyclic amines have extensive use. Derivatives of the cyclic amines are very useful compounds which are widely used in various industrial fields as, for example, textile finishing agents, antistatic agents, and materials for medicines and agricultural chemicals.

The present invention provides a catalyst of high performance for use in the production of such useful cyclic amines by the intramolecular dehydration reaction of alkanolamines in the vapor-phase which is very advantageous in regard to productivity.

Known methods of converting alkanolamines into cyclic amines by dehydration reaction include, for example, the intramolecular cyclization of haloalkylamines with concentrated alkalies (Gabriel method), and cyclization of alkanolamine sulfuric acid esters with hot concentrated alkalies (Wenker method). These methods, however, are not industrially satisfactory because the use of large amounts of alkalies as a concentrated solution reduces productivity and increases the percentages of the cost of the alkalies in the total expenditure of raw materials, and large amounts of inorganic salts of low utilitarian values are formed as by-products.

In recent years, some attempts at dehydration reaction of monoethanolamine as the alkanolamine in the vapor phase in the presence of a catalyst to produce the corresponding cyclic amine, i.e. ethylenimine, continuously have been reported in contrast to the above liquid-phase methods. For example, Chemical Abstracts, 83, 163983 discloses the use of a tungsten oxide-type catalyst; U.S. Pat. No. 4,301,036 discloses the use of a catalyst comprising tungsten oxide and silicon; and U.S. Pat. Nos., 4,289,656, 4,337,175 and 4,477,591 disclose the use of niobium- or tantalum-type catalysts. With any of these catalysts, the conversion of monoethanolamine is low. Even when this conversion is relatively high, the proportion of products of side-reactions such as deammoniation reaction, and dimerization reaction is high, and the selectivity of ethylenimine is low. Investigations of the present inventors have shown that these catalysts are deteriorated markedly within short periods of time, and are quite unsatisfactory in industrial practice.

The present inventors have extensively worked on a catalyst for the vapor-phase intramolecular dehydration reaction of alkanolamines, and have found that by using an oxide catalyst represented by the general formula $$X_a P_b Y_c O_d$$

wherein X is at least one element selected from alkali metals and alkaline earth metals, P is phosphorus, Y is at least one element selected from B, Al, Si, S, Sc, Ti, Cu, Y, Zr, Nb, Mo, Sn, Sb, La, Ce, Ta, W, Tl, Pb, Bi and Th, O is oxygen, the suffixes a, b, c and d represent atomic ratios of the elements X, P, Y and O, and when a=1, b=0.01–3 (preferably 0.05–2) and c=0–100 (preferably 0.01–50) and d is a value determined by a, b and c and the state of bonding of the constituent elements, alkanolamines can be very conveniently dehydrated intramolecularly in the vapor phase to give the desired cyclic amines in high selectivities and high yields stably over a long period of time.

In the vapor-phase intramolecular dehydration reaction in which the catalyst of this invention is used, alkanolamines represented by the general formula

wherein R and R' are each selected from hydrogen, a methyl group and an ethyl group, and n is an integer of 2 to 5, are suitable as the starting material. Specific examples of the alkanolamines are (a) monoethanolamine, (b) isopropanolamine, (c) 3-amino-1-propanol, (d) 5-amino-1-pentanol, and (e) 2-amino-1-butanol. These examples, however, are not limitative.

These alkanol amines are converted to cyclic amines of the general formula

wherein R, R' and n are as defined for formula (I), by using the catalyst of this invention. For example the compound (a) is converted into ethylenimine; the compound (b), into 2-methyl-ethylenimine; the compound (c), into azetidine; the compound (d), into piperidine; and the compound (e), into 2-ethyl-ethylenimine, all in high conversions and high selectivities stably over long periods of time.

Raw materials used for preparation of the catalyst of this invention are as follows. As sources of X and Y components, their metals and their oxides, hydroxides, halides, nitrates, carbonates, sulfates and phosphates may be used. As a source of phosphorus, there may be used various phosphoric acids such as orthophosphoric acid, pyrophosphoric acid, meta-phosphoric acid, phophorous acid and polyphosphoric acid, salts of these phosphoric acids, and phosphorus pentoxide.

There is no particular limitation on a method of preparing the catalyst of this invention, and ordinary methods may be used. For example, there may be used (1) a method which comprises dissolving or suspending raw materials for X component and phosphorus in water, concentrating the solution or suspension by heating with stirring, drying the concentrate, molding it and calcining it, (2) a method which comprises dissolving or suspending the raw materials for component X and phosphorus in water, drying the concentrate, adding a raw material for component Y, kneading them together with a suitable molding aid (such as water or alcohol), drying the mixture, and calcining it, and (3) a method which comprises dissolving or suspending raw materials for component X, phosphorus and component Y in water, concentrating the solution or suspension by heating with stirring, drying the concentrate and calcining and molding it.

Some catalysts prepared as above may have a low surface area and low activity, or wettability, or low mechanical strength. Such catalysts exhibit their inherent high performance by supporting them on suitable solid carriers. The suitable amount of the catalytically active component (oxide composition) based on the carrier differs depending upon the type and properties of the carrier, but is usually adjusted to 1 to 60% based on the weight of the finished catalyst. If the carrier has a high surface area, larger amounts (e.g., 40 to 60%) of deposition on the carrier within the above-specified range lead to higher selectivity. On the other hand, if the carrier has a low surface area, large amounts of deposition reduce the activity of the catalyst. If a molded carrier or a powdery carrier is used, the suitable amount of deposition also varies depending upon its pore diameter or particle size, respectively. The amount of deposition should therefore be properly selected according to the carrier used. Examples of suitable carriers include diatomaceous earth, silica gel, alumina, silicaalumina, silicon carbide, silicon nitride, zirconia, clay minerals (e.g., kaolin, bentonite, montmorillonite, etc.) and calcium hydroxyapatite.

The calcination temperature for the catalyst, which may be varied depending upon the types of the raw materials used, is 300° to 1,500° C., preferably 400° to 1,200° C.

The catalyst of this invention shows much higher activity than conventional known catalysts in the vapor-phase intramolecular dehydration reaction of alkanolamines. The selectivity of the desired cyclic amine is very high. Even when this reaction is continuously carried out for a long period of time, the catalyst of this invention does not show an appreciable deterioration in activity. Accordingly, the problem of deterioration within a short time, which is most cumbersome in industrial practice, can be fully overcome by the catalyst of this invention.

Incidentally, it has further been found that the activity and selectivity of the catalysts of this invention are much higher than those of known catalysts for synthesis of ethylenimine from monoethanolamine (for example, the $WO_3$-$SiO_2$ catalyst and the $Nb_2O_5$-$BaO$ catalyst disclosed respectively in Chemical Abstracts, 83, 163883 and U.S. Pat. No. 4,337,175).

No detailed reason has yet been able to be assigned to the fact that the catalyst of this invention exhibits very superior performance in the vapor-phase dehydration reaction of alkanolamines to cyclic amines. However, it may be theorized as follows:- The alkanolamine has the $—NH_2$ and $—OH$ groups. There is polarization between these polar substituent groups and the carbons to which they are bonded, and these substituent groups are very active on the catalyst. Hence, the cooperative action of a weak acid site and a weak basic site is considered to be effective in carrying out the intramolecular dehydration reaction of the alkanolamines efficiently. The catalyst of this invention contains an alkali metal or alkaline earth metal phosphate, and a basic site based on a bridging oxygen between the metal and phosphorus and oxygen having a double bond on phosphorus and an acid site based on the metal and phosphorus exist in the phosphate. The acid and basic sites act effectively on the intramolecular dehydration reaction of the alkanolamines. As a result, the following advantages can be obtained.

(1) The cooperative action of the acid and base promotes the reaction of hydrogen extraction from the amino group on the basic site and the reaction of hydroxyl extraction on the acid site.

(2) The basic site expedites desorption of the resulting cyclic amine from the catalyst surface, and a consecutive polymerization reaction or decomposition reaction is inhibited.

(3) The component Y controls the acid and basic sites qualitatively and quantitatively.

(4) Sometimes, by the use of the carrier, the physical properties such as the surface area, pore diameter or pore volume, of the catalyst are improved.

By measurement with indicator chemicals, the catalysts of this invention have been found to have a very weak acid and base strength near neutrality.

The reaction for use in carrying out the vaporphase intramolecular dehydration reaction of alkanolamines using the catalyst of this invention may be of a fixed bed type, a fluidized bed type or a moving bed type. As required, the starting alkanolamine may be diluted with an inert gas such as nitrogen, helium or argon to a concentration of 1 to 80% by volume, preferably 2 to 50% by volume, prior to submitting to the reaction. To inhibit side reactions, ammonia or water may be fed together with the alkanolamine. The reaction can usually be carried out under atmospheric pressure, but as required, it may be carried out under elevated or reduced pressure. The reaction temperature, which varies depending upon the types of the starting material, is within the range of 300° to 600° C. The suitable space velocity of the starting gas, which varies depending upon the type of the starting material and the concentration of the starting material, is 100 to 40,000 $hr^{-1}$, preferably 500 to 20,000 $hr^{-1}$.

The following examples illustrate the present invention more specifically. In these examples, the conversion, selectivity and one-pass yield are used in accordance with the following definitions.

Conversion (mole %) =

$\frac{\text{Moles of the alkanolamine consumed}}{\text{Moles of the alkanolamine fed}} \times 100$ Selectivity (mole %) =

$\frac{\text{Moles of the cyclic amine formed}}{\text{Moles of the alkanolamine consumed}} \times 100$ -continued One-pass yield (mole %) =

$$\frac{\text{Moles of the cyclic amine formed}}{\text{Moles of the alkanolamine fed}} \times 100$$

EXAMPLE 1

Lithium hydroxide (23.9 g) was dissolved in 200 ml of water, and the solution was heated at 90° C. With stirring, 34.5 g of 85% by weight phosphoric acid was added. The mixture was further heated with stirring to concentrate it and obtain a white precipitate. The precipitate was transferred to a stainless steel vat, dried at 120° C., calcined in air at 600° C. for 2 hours and pulverized to a size of 3.5 mesh to prepare a catalyst.

Twenty milliliters of the catalyst was filled in a stainless steel reaction tube having an inside diameter of 16 mm, and then the reaction tube was immersed in a molten salt bath at 340° C. A starting gaseous mixture consisting of monoethanolamine and nitrogen in a volume ratio of 5:95 was passed through the reaction tube at a space velocity of 1,500 hr$^{-1}$, and the reaction product was analyzed by gas chromatography. The results are shown in Table 1.

EXAMPLE 2

Magnesium oxide (20.0 g) was suspended in 100 ml of water, and while the suspension was heated at 90° C. with stirring, 57.6 g of 85% by weight phosphoric acid was added. The mixture was concentrated. The resulting slurry-like material was dried at 120° C., calcined at 600° C. for 2 hours in air, and then pulverized to a size of 3.5 mesh to prepare a catalyst.

Using the resulting catalyst, monoethanolamine and 5-amino-1-pentanol were reacted respectively as in Example 1. The results are shown in Table 1.

EXAMPLE 3

Calcium nitrate tetrahydrate (118.1 g) was dissolved in 200 ml of water. The solution was heated at 80° C., and with stirring, a solution of 33 g of diammonium phosphate in 100 ml of water was added. Thereafter, aqueous ammonia was added to maintain the pH of the solution basic, and the solution was aged for 30 minutes, cooled, filtered, and washed with water to give a white solid. The solid was dried at 120° C., calcined at 600° C. for 2 hours in a stream of air, and pulverized to a size of 3.5 mesh to prepare a catalyst.

Using the resulting catalyst, monoethanolamine and isopropanolamine were reacted respectively as in Example 1. The results are shown in Table 1.

EXAMPLE 4

A catalyst was prepared in the same way as in Example 2 except that 79.7 g of strontium hydroxide octahydrate and 24.2 g of 85% by weight phosphoric acid were used as the raw materials. Using the resulting catalyst, monoethanolamine and 2-amino-1-butanol were reacted respectively as in Example 1. The results are shown in Table 1.

EXAMPLE 5

A catalyst was prepared in the same way as in Example 2 except that 63.1 g of barium hydroxide octahydrate and 18.5 g of diammonium phosphate were used as the raw materials. Using the resulting catalyst, monoethanolamine and 3-amino-1-propanol were reacted respectively as in Example 1. The results are shown in Table 1.

EXAMPLE 6

A catalyst was prepared in the same way as in Example 2 except that 63.1 g of barium hydroxide octahydrate and 65.9 g of magnesium phosphate docosahydrate were used as the raw materials. Using the resulting catalyst, monoethanolamine and 5-amino-1-propanol were reacted respectively as in Example 1. The results are shown in Table 1.

EXAMPLE 7

Calcium nitrate tetrahydrate (118.1 g) was dissolved in 200 ml of water. While the solution was heated at 80° C. with stirring, a solution of 107.4 g of disodium hydrogen phosphate dodecahydrate in 200 ml of water was added to the solution. Aqueous ammonia was added to maintain the pH of the solution basic, and the solution was aged for 1 hour, and cooled. The precipitate was collected by filtration and washed with water to give a white solid. The solid was dried at 120° C., calcined at 500° C. for 2 hours in an air stream, and pulverized to a size of 3.5 mesh to prepare a catalyst.

Fluorescent X-ray analysis led to the determination that sodium remained in the catalyst.

Using the resulting catalyst, monoethanolamine as reacted as in Example 1. The results are shown in Table 1.

EXAMPLE 8

Using the same catalyst as in Example 7, a starting gaseous mixture consisting of monoethanolamine and nitrogen in a volume ratio of 10:90 was introduced into a reactor and continuously reacted at a reaction temperature of 390° C. substantially under the reaction conditions described in Example 1. The results obtained 2 hours after the start of the reaction and 200 hours (reaction temperature 400° C.) after the start of the reaction are shown in Table 1.

EXAMPLE 9

Strontium hydroxide octahydrate (79.7 g) was suspended in 200 ml of water, and while the suspension as heated at 90° C. with stirring, 5.8 g of 85% by weight phosphoric acid was added. The mixture was stirred further for 30 minutes, and then 30.0 g of cesium hydroxide was added. The mixture was concentrated, dried at 120° C., calcined at 400° C. for 2 hours in air and pulverized to a size of 3.5 mesh to prepare a catalyst.

Using the resulting catalyst, monoethanolamine was reacted as in Example 1. The results are shown in Table 1.

EXAMPLE 10

Silicon dioxide (30 g) was dispersed in 150 ml of water, and while the dispersion was heated with stirring, 1.20 g of lithium hydroxide and 0.29 g of 85% by weight phosphoric acid were added. The mixture was concentrated by heating to give a white slurry. The slurry was dried overnight at 120° C. in air, calcined at 600° C. for 2 hours in air, and pulverized to a size of 3.5 mesh to prepare a catalyst.

A starting gas consisting of monoethanolamine and nitrogen in a volume ratio of 10:90 was introduced into the reactor and monoethanolamine was continuously reacted as in Example 1 except that the resulting catalyst was used and the reaction temperature was changed to 400° C. The products obtained 2 hours (reaction temperature 400° C.) and 200 hours (reaction temperature 420° C.) after the start of the reaction were quantitatively analyzed by gas chromatography. The results are shown in Table 2.

EXAMPLE 11

Silicon dioxide (24 g) and 0.087 g of boron oxide were well mixed in the form of a powder in a mortar, and 4.25 g of sodium nitrate and 2.88 g of 85 % by weight phosphoric acid were put in it. They were kneaded while adjusting its moisture content with water. The wet solid obtained was dried, calcined and pulverized to a size of 3.5 mesh as in Example 1.

Using the resulting catalyst, monoethanolamine and isopropanolamine were reacted respectively as in Example 10. The results are shown in Table 2.

EXAMPLE 12

Barium hydroxide octahydrate (63.1 g) and 5.28 g of ammonium phosphate were put in 100 ml of water. While the mixture was heated with stirring, 0.392 g of 98% by weight sulfuric acid was added. The mixture was further heated with stirring to obtain a white slurry-like material. It was dried overnight at 120° C. in air, calcined at 600° C. for 2 hours in air, and pulverized to a size of 3.5 mesh to prepare a catalyst.

Using the resulting catalyst, monoethanolamine and 2-amino-1-butanol were reacted respectively as in Example 10. The results are shown in Table 2.

EXAMPLE 13

Cesium carbonate (11.40 g), 9.24 g of ammonium phosphate, 1.74 g of magnesium hydroxide, 2.66 g of thallium nitrate and 25.5 g of aluminum oxide were heated with stirring in 200 ml of water to form a white slurrylike material. It was dried overnight at 120° C. in air, calcined at 700° C. for 3 hours in air, and pulverized to prepare a catalyst.

Using the resulting catalyst, monoethanolamine and 3-amino-1-propanol were reacted respectively as in Example 10. The results are shown in Table 2.

EXAMPLE 14

Calcium hydroxide (29.7 g), 26.4 g of ammonium phosphate, 0.54 g of stannic oxide, 0.58 g of antimony trioxide and 20 ml of waterwere kneaded in a mortar. The mixture was dried, calcined and pulverized as in Example 1 to prepare a catalyst.

Using the resulting catalyst, monoethanolamine and 2-amino-1-butanol were reacted respectively as in Example 10. The results are shown in Table 2.

EXAMPLE 15

Barium hydroxide octahydrate (31.55 g) and 6.6 g of ammonium phosphate were heated with stirring in 100 ml of water and concentrated. The concentrate was transferred to a mortar and 0.82 g of lanthanum oxide and 0.44 g of bismuth oxide were added. They were well kneaded, and the mixture was dried, calcined and pulverized as in Example 1 to prepare a catalyst.

Using the resulting catalyst, monoethanolamine and 3-amino-1-propanol were reacted respectively under the reaction conditions indicated in Table 2. The results are shown in Table 2.

EXAMPLE 16

Rubidium hydroxide (4.1 g) and 42.5 g of strontium hydroxide octahydrate were suspended in 100 ml of water, and while the suspension was heated with stirring, 6.92 g of 85% by weight phosphoric acid, 2.21 g of thorium nitrate tetrahydrate and 3.31 g of lead nitrate were added, and the mixture was concentrated by heating to give a white slurry-like substance. The slurry-like material was dried overnight at 120° C. in air, calcined at 800° C. for 2 hours in air, and pulverized to a size of 3.5 mesh to prepare a catalyst.

Using the resulting catalyst, monoethanolamine was reacted continuously as in Example 10. The results are shown in Table 2.

EXAMPLE 17

Tricalcium phosphate (31.02 g) and 17.42 g of dipotassium phosphate were suspended in 200 ml of water, and while the suspension was heated with stirring, 3.44 g of cerium oxide was added. The mixture was concentrated by heating, and thereafter dried, calcined and pulverized as in Example 1 to prepare a catalyst.

Using the resulting catalyst, monoethanolamine and 5-amino-1-pentanol were reacted respectively as in Example 10. The results are shown in Table 2.

EXAMPLE 18

The same reaction as in Example 10 was carried out except that the same catalyst as in Example 17 was used, a starting gaseous mixture consisting of monoethanolamine and nitrogen in a volume ratio of 10:90 was passed at a space velocity of 14,000 $hr^{-1}$, and the reaction temperature was changed to 470° C.

EXAMPLE 19

Silicon dioxide (30 g) and 0.58 g of barium phosphate were mixed in a powdery form, and then a solution of 0.82 g of cesium carbonate and 0.86 g of 85% by weight phosphoric acid in 30 ml of water was added. These materials were well kneaded. The resulting mixture was dried overnight at 120° C. in air, calcined at 850° C. for 2 hours in air, and pulverized to a size of 3.5 mesh to prepare a catalyst.

Using the resulting catalyst, monoethanolamine was continuously reacted as in Example 10. The results are shown in Table 2.

EXAMPLE 20

Titanium dioxide (28.0 g) and 0.345 g of scandium oxide were suspended in 100 ml of water, and while the suspension was heated with stirring, 8.953 g of disodium phosphate dodecahydrate was added. The mixture was concentrated to obtain a white slurry-like material. It was then dried, calcined, and pulverized as in Example 1 to prepare a catalyst.

Using the resulting catalyst, monoethanolamine was reacted as in Example 10. The results are shown in Table 3.

EXAMPLE 21

A solution of 4.89 g of cesium nitrate and 2.42 g of 85 % by weight phosphoric acid in 30 ml of water was added to 23.97 g of titanium dioxide, and the mixture was well kneaded. Then, 0.338 g of yttrium oxide was added, and the entire mixture was further kneaded. The resulting mixture was dried overnight at 120° C. in air, calcined at 850° C. for 2 hours in air, and pulverized to a size of 3.5 mesh to prepare a catalyst.

Using the resulting catalyst, monoethanolamine and isopropanolamine were reacted as in Example 10. The results are shown in Table 3.

EXAMPLE 22

Barium chloride dihydrate (24.43 g) was dissolved in 100 ml of water, and while the solution was heated with stirring, a solution of 13.20 g of ammonium phosphate in 100 ml of water was added. Thereafter, aqueous ammonia was added to adjust the pH of the solution to 8 to 10, and the solution was further stirred for 1 hour. The resulting precipitate was collected by filtration, and washed with water. To the resulting white solid was added 0.18 g of ammonium molybdate tetrahydrate, and the mixture was well kneaded in a mortar. The mixture was dried, calcined and pulverized as in Example 1 to prepare a catalyst.

Using the resulting catalyst, monoethanolamine and 3-amino-1-propanol were reacted respectively as in Example 10. The results are shown in Table 3.

EXAMPLE 23

Niobium pentoxide (26.58 g) was suspended in 100 ml of water, and while the suspension was heated with stirring, a solution of 0.024 g of lithium hydroxide and 0.922 g of rubidium hydroxide in 50 ml of water was added. Thereafter, 0.462 g of 85 % by weight phosphoric acid and 0.121 g of copper nitrate trihydrate were added, and the mixture was concentrated to dryness. The resulting solid was calcined at 750° C. for 2 hours in air, and pulverized to a size of 3.5 mesh.

Using the resulting catalyst, monoethanolamine and 5-amino-1-pentanol were reacted respectively as in Example 10. The results are shown in Table 3.

EXAMPLE 24

A suspension of 1.52 g of potassium nitrate, 2.03 g of magnesium hydroxide and 6.60 g of ammonium phosphate in 30 ml of water was kneaded with 33.1 g of tantalum oxide and 0.089 g of ammonium molybdate tetrahydrate in a mortar. The resulting mixture was dried, calcined, and pulverized as in Example 1 to prepare a catalyst.

Using the resulting catalyst, monoethanolamine and 2-amino-1-butanol were reacted respectively as in Example 10. The results are shown in Table 3.

EXAMPLE 25

Zirconium oxide (24.64 g) and 8.33 g of tungstic acid were suspended in 100 ml of water, and while the suspension was heated with stirring, 0.5 g of calcium hydroxide and 0.62 g of ammonium phosphate were added. The mixture was concentrated to obtain a slurry-like material. The slurry-like material was dried overnight at 120° C. is air, calcined at 800° C. C. for 3 hours in air, and pulverized to a size of 3.5 mesh to prepare a catalyst.

Using the resulting catalyst, monoethanolamine was reacted as in Example 10. The results are shown in Table 3.

EXAMPLE 26

Cesium carbonate (0.65 g), 0.45 g of strontium hydroxide octahydrate and 0.40 g of 85% by weight phosphoric acid were added to 24.64 g of zirconium nitrate. The mixture was kneaded in a mortar together with 30 ml of water. The resulting mixture was dried, calcined and pulverized as in Example 1 to prepare a catalyst.

Using the resulting catalyst, monoethanaolamine and isopropanolamine were reacted under the reaction conditions indicated in Table 3. The results are shown in Table 3.

EXAMPLE 27

A mixture of 1.35 g of cesium hydroxide, 0.32 g of barium hydroxide octahydrate and 0.69 g of 85% by weight phosphoric acid with 30 ml of water was added to a mixture of 24.64 g of zirconium oxide and 0.08 g of titanium dioxide, and they were kneaded in a mortar. The resulting mixture was then dried, calcined, and pulverized as in Example 1 to prepare a catalyst.

Using the resulting catalyst, monoethanolamine was reacted as in Example 10. The results are shown in Table 3.

EXAMPLE 28

Thirty grams of diatomaceous earth (Celite, tradename) and 15 g of disodium phosphate dodecahydrate were suspended in 100 ml of water, and the suspension was concentrated by heating with stirring to obtain a slurrylike substance. The resulting mixture was dried, calcined and pulverized as in Example 1 to prepare a catalyst.

Using the resulting catalyst, monoethanolamine was reacted as in Example 10. The results are shown in Table 4.

EXAMPLE 29

Zirconia (30.8 g) was suspended in 100 ml of water, and while the suspension was heated with stirring, 0.414 g of scandium oxide was added. Then, a solution of 10.7 g of sodium phosphate dodecahydrate in 50 ml of water was added, and the mixture was concentrated by heating. The resulting solid was dried overnight at 120° C. in air, calcined at 700° C. for 2 hours, and pulverized to a size of 3.5 mesh to prepare a catalyst.

Using the resulting catalyst, monoethanolamine was reacted continuously as in Example 10. The results are shown in Table 4.

EXAMPLE 30

One hundred grams of silica gel powder, 0.024 g of boron oxide and 0.112 g of titanium oxide were well mixed in a mortar, and then a solution of 7.18 g of rubidium hydroxide and 2.42 g of 85% by weight phosphoric acid in 30 ml of water was added, and the materials were kneaded. The resulting mixture was dried, calcined and pulverized as in Example 1 to prepare a catalyst.

Using the resulting catalyst, monoethanolamine and isopropanolamine were reacted as in Example 10. The results are shown in Table 4.

EXAMPLE 31

Twenty grams of calcium hydroxyapatite, 0.80 g of niobium pentoxide and 0.13 g of lanthanum oxide were well mixed in a mortar. Then, a solution of 6.52 g of cesium carbonate and 3.23 g of 85% by weight phosphoric acid in 30 ml of water was added, and then these materials were kneaded. The resulting mixture was dried, calcined, and pulverized as in Example 1 to prepare a catalyst.

Using the resulting catalyst, monoethanolamine and 5-amino-1-pentanol were reacted as in Example 10. The results are shown in Table 4.

EXAMPLE 32

Calcium hydroxide (6.34 g) and 11.22 g of potassium hydroxide were suspended in 100 ml of water, and while the suspension was heated with stirring, 15.09 g of ammonium phosphate, 2.57 g of silicon oxide and 0.146 g of aluminum oxide were added. The mixture was concentrated by heating, and then calcined at 500° C. for 6 hours in air. A portion (13 g) of the resulting solid was kneaded in a mortar together with 20 g of potassium titanate and 30 ml of water. The mixture was dried overnight at 120° C. in air, calcined at 800° C. for 2 hours, and then pulverized to a size of 3.5 mesh to prepare a catalyst.

Using the resulting catalyst, monoethanolamine and 2-amino-1-butanol were reacted respectively as in Example 10. The results are shown in Table 4.

EXAMPLE 33

Sodium nitrate (1.46 g), 2.32 g of magnesium hydroxide and 3.96 g of 85% by weight phosphoric acid were suspended in 50 ml of water, and while the suspension was heated with stirring, 0.138 g of copper nitrate trihydrate and 0.168 g of 98% by weight sulfuric acid were added. The mixture was concentrated to dryness. The concentrate was then calcined at 500° C. for 3 hours in air. A portion (6.7 g) of the resulting solid was kneaded in a mortar together with 20 g of silica-alumina and 30 ml of water. The kneaded mixture was dried overnight at 120° C. in air, calcined at 800° C. for 2 hours, and pulverized to a size of 3.5 mesh.

Using the resulting catalyst, monoethanolamine and 3-amino-1-propanol were reacted as in Example 10. The results are shown in Table 4.

EXAMPLE 34

Zirconia (20 g), 0.159 g of tantalum oxide and 0.167 g of tungsten oxide were well mixed in a mortar, and then 2.70 g of cesium hydroxide and 3.10 g of calcium hydrogen phosphate dihydrate were added. The mixture was kneaded together with 30 ml of water. The resulting mixture was dried overnight at 120° C. in air, calcined at 700° C. for 3 hours, and pulverized to a size of 3.5 mesh to prepare a catalyst.

Using the resulting catalyst, monoethanolamine was reacted under the reaction conditions indicated in Table 4. The results are shown in Table 4.

EXAMPLE 35

Disodium phosphate dodecahydrate (14.33 g) and 1.17 g of magnesium hydroxide were suspended in 50 ml of water, and the suspension was concentrated by heating with stirring. The concentrate was calcined at 600° C. in air for 2 hours. A portion (4.87 g) of the resulting solid was kneaded in a mortar together with 0.172 g of cerium oxide, 0.986 g of zirconium oxide, 20 g of silicon nitride and 30 ml of water. The resulting mixture was dried overnight at 120° C. in air, calcined at 800° C. for 2 hours, and pulverized to a size of 3.5 mesh to prepare a catalyst.

Using the resulting catalyst, monoethanolamine and isopropanolamine were reacted respectively as in Example 10. The results are shown in Table 4.

EXAMPLE 36

Rubidium hydroxide (4.10 g), 2.34 g of barium hydrogen phosphate and 1.98 g of ammonium phosphate were heated in 50 ml of water with stirring, and 0.113 g of yttrium oxide and 0.408 g of lanthanum oxide were added. Thereafter, 20 g of alpha-alumina (Norton SA5218, 3.5 mm in diameter) was added, and the mixture was heated with stirring. The product was dried overnight at 120° C. in air, and calcined at 700° C. for 3 hours. The ratio of deposition in this catalyst was about 20% by weight.

Using the resulting catalyst, monoethanolamine was reacted continuously as in Example 10. The results are shown in Table 4.

EXAMPLE 37

Potassium hydroxide (0.249 g), 6.0 g of cesium hydroxide and 3.07 g of 85% by weight phosphoric acid were dissolved in 100 ml of water. While the solution was heated with stirring, 0.077 g of boron oxide and 0.245 g of thorium nitrate tetrahydrate were added. The mixture was concentrated to a slurry. The slurry was then calcined at 1000° C. in air, and pulverized. The powder (6.7 g) and 20 g of silicon carbide powder were kneaded with 30 ml of water. The resulting mixture was dried overnight at 120° C. in air, calcined at 800° C. for 2 hours, and pulverized to a size of 3.5 mesh to prepare a catalyst.

Using the resulting catalyst, monoethanolamine was reacted continuously as in Example 10. The results are shown in Table 4.

COMPARATIVE EXAMPLE 1

Silicon carbide having a particle diameter of 5 mm (40 g) was immersed in 65.2 g of an aqueous solution of ammonium meta-tungstate (50% by weight as $WO_3$), and evaporated over a hot water bath. The product was dried at 150° C. for 1 hour in air, and calcined at 715° C. in air for 4 hours to prepare a catalyst precursor. The precursor was immersed in 50 ml of a 10% colloidal solution of silicon dioxide, and evaporated to dryness over a hot water bath. The product was dried at 150° C. for 1 hour in air, and subsequently calcined at 715° C. for 4 hours to give a supported catalyst ($W_{1.0}Si_{0.5}O_{4.1}$ in atomic ratio) containing 25.4% by weight of tungsten oxide and 3.3% by weight of silicon dioxide.

Using the resulting catalyst, monoethanolamine was reacted as in Example 1. The results are shown in Table 5.

This catalyst was prepared in accordance with Example 4 of U.S. Pat. No. 4,301,036.

COMPARATIVE EXAMPLE 2

Niobium pentachloride (5.0 g) was completely dissolved in 50 ml of water at 60° C. Aqueous ammonia was added to adjust the pH of the solution to 7.0. The solution was filtered, and washed with water. The resulting solid was dissolved in 80 ml of a 10% by weight aqueous solution of oxalic acid. Furthermore, 0.2 g of barium hydroxide octahydrate was added. Silicon carbide (60 ml) was immersed in the solution, and the mixture was evaporated to dryness at 80° C. The resulting product was calcined at 500° C. in air for 3 hours to give a supported catalyst containing 3.7% by weight of niobium pentoxide and 0.5% by weight of barium oxide ($Nb_{1.0}Ba_{0.1}O_{2.6}$ by atomic ratio). Using this catalyst, monoethanolamine was reacted under the reaction conditions described in Example 1. The results are shown in Table 5.

This catalyst was prepared in accordance with Example 3 of U.S. Pat. No. 4,477,591.

TABLE 1

| Example | Catalyst composition (atomic ratio excepting oxygen) X | P | Starting alkanolamine (I) | Produced cyclic amine (II) | Reaction temperature (°C.) | Concentration of the starting alkanolamine (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|
| 1 | Li = 1 | 0.3 | mono-ethanol-amine | ethylen-imine | 340 | 5 | 2 | 42.2 | 67.1 | 28.3 |
|  |  |  |  |  | 340 |  | 500 | 41.9 | 69.6 | 29.2 |
| 2 | Mg = 1 | 1.0 | mono-ethanol-amine | ethylen-imine | 340 | 5 | 2 | 38.5 | 64.7 | 24.9 |
|  |  |  | 5-amino-1-pentanol | piperi-dine | 330 | 5 | 2 | 47.1 | 69.4 | 32.7 |
| 3 | Ca = 1 | 0.5 | mono-ethanol-amine | ethylen-imine | 360 | 5 | 2 | 60.2 | 81.3 | 48.9 |
|  |  |  | iso-propanol-amine | 2-ethyl-ethylen-imine | 340 | 5 | 2 | 65.7 | 74.6 | 49.0 |
| 4 | Sr = 1 | 0.7 | mono-ethanol-amine | ethylen-imine | 330 | 5 | 2 | 41.6 | 79.8 | 33.2 |
|  |  |  | 2-amino-1-butanol | 2-ethyl-ethylen-imine | 320 | 5 | 2 | 52.3 | 71.6 | 37.4 |
| 5 | Ba = 1 | 0.7 | mono-ethanol-amine | ethylen-imine | 330 | 5 | 2 | 48.5 | 77.1 | 37.4 |
|  |  |  | 3-amino-1-propanol | azetidine | 340 | 5 | 2 | 50.6 | 71.9 | 36.4 |
| 6 | Mg = 0.6 | 0.4 | mono-ethanol-amine | ethylen-imine | 350 | 5 | 2 | 60.9 | 81.5 | 49.6 |
|  | Ba = 0.4 |  | 5-amino-1-pentanol | piperi-dine | 330 | 5 | 2 | 65.6 | 74.9 | 49.1 |
| 7 | Ca = 0.9 Na = 0.1 | 0.5 | mono-ethanol-amine | ethylen-imine | 340 | 5 | 2 | 70.8 | 88.2 | 62.4 |
| 8 | Ca = 0.9 Na = 0.1 | 0.5 | mono-ethanol-amine | ethylen-imine | 390 | 10 | 2 | 71.8 | 70.0 | 50.3 |
|  |  |  |  |  | 400 |  | 200 | 70.2 | 70.5 | 49.5 |
| 9 | Sr = 0.6 Cs = 0.4 | 0.1 | mono-ethanol-amine | ethylen-imine | 290 | 5 | 2 | 39.9 | 91.4 | 36.5 |

TABLE 2

| Example | Catalyst composition (atomic ratio excepting oxygen) X | P | Y | Starting alkanolamine (I) | Produced cyclic amine (II) | Reaction temperature (°C.) | Concentration of the starting alkanolamine (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|---|
| 10 | Li = 1 | 0.05 | Si = 10 | mono-ethanol-amine | ethylen-imine | 400 | 10 | 2 | 49.3 | 65.1 | 32.1 |
|  |  |  |  |  |  | 420 |  | 200 | 47.9 | 66.6 | 31.9 |
| 11 | Na = 1 | 0.5 | Si = 8 | mono-ethanol-amine | ethylen-imine | 400 | 10 | 2 | 56.9 | 73.8 | 42.0 |
|  |  |  | B = 0.05 | iso-propanol-amine | 2-methyl-ethylen-imine | 400 | 10 | 2 | 63.8 | 77.2 | 49.3 |
| 12 | Ba = 1.0 | 0.2 | S = 0.1 | mono-ethanol-amine | ethylen-imine | 410 | 10 | 2 | 70.4 | 82.1 | 57.8 |
|  |  |  |  | 2-amino-1-butanol | 2-ethylen-imine | 400 | 10 | 2 | 71.3 | 83.8 | 59.7 |
| 13 | Mg = 0.3 | 0.7 | Tl = 0.1 | mono-ethanol-amine | ethylen-imine | 410 | 10 | 2 | 61.3 | 83.6 | 51.2 |
|  | Cs = 0.7 |  | Al = 5.0 | 3-amino-1-propanol | azetidine | 400 | 10 | 2 | 52.9 | 84.2 | 44.5 |
| 14 | Ca = 1.0 | 0.5 | Sn = 0.01 | mono-ethanol- | ethylen-imine | 390 | 10 | 2 | 72.6 | 81.6 | 59.2 |

TABLE 2-continued

| Example | Catalyst composition (atomic ratio excepting oxygen) X | P | Y | Starting alkanolamine (I) | Produced cyclic amine (II) | Reaction temperature (°C.) | Concentration of the starting alkanolamine (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|---|
| | | | Sb = 0.01 | amine 2-amino-1-butanol | 2-ethyl-ethylen-imine | 390 | 10 | 2 | 75.3 | 82.4 | 62.0 |
| 15 | Ba = 1 | 0.5 | La = 0.05 | mono-ethanol-amine | ethylen-imine | 400 | 20 | 2 | 56.7 | 80.0 | 45.4 |
| | | | Bi = 0.01 | 3-amino-1-propanol | azetidine | 400 | 20 | 2 | 50.4 | 84.8 | 42.7 |
| 16 | Rb = 0.2 Sr = 0.8 | 0.3 | Th = 0.02 Pb = 0.05 | mono-ethanol-amine | ethylen-imine | 400 400 | 10 10 | 2 200 | 80.9 80.1 | 79.3 79.6 | 64.2 63.8 |
| 17 | K = 0.4 Ca = 0.6 | 0.6 | Ce = 0.04 | mono-ethanol-amine | ethylen-imine | 390 | 10 | 2 | 86.4 | 72.1 | 62.3 |
| | | | | 5-amino-1-pentanol | piperi-dine | 390 | 10 | 2 | 88.8 | 76.9 | 68.3 |
| 18 | K = 0.4 Ca = 0.6 | 0.6 | Ce = 0.04 | mono-ethanol-amine | ethylen-imine | 470 | 10 | 2 | 52.1 | 83.3 | 43.4 |
| 19 | Ba = 0.5 Cs = 0.5 | 1.0 | Si = 50 | mono-ethanol-amine | ethylen-imine | 410 420 | 10 10 | 2 500 | 83.4 81.0 | 85.2 86.0 | 70.2 69.7 |

TABLE 3

| Example | Catalyst composition (atomic ratio excepting oxygen) X | P | Y | Starting alkanolamine (I) | Produced cyclic amine (II) | Reaction temperature (°C.) | Concentration of the starting alkanolamine (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|---|
| 20 | Na = 1 | 0.5 | Sc = 0.1 Ti = 7 | mono-ethanol-amine | ethylen-imine | 390 400 | 10 | 2 200 | 78.2 78.0 | 76.6 76.4 | 59.9 59.6 |
| 21 | Cs = 1 | 0.7 | Y = 0.1 | mono-ethanol-amine | ethylen-imine | 400 | 10 | 2 | 81.4 | 79.2 | 64.5 |
| | | | Ti = 10 | iso-propanol-amine | 2-methyl-ethylen-imine | 400 | 10 | 2 | 83.3 | 81.6 | 68.0 |
| 22 | Ba = 1.0 | 1.0 | Mo = 0.01 | mono-ethanol-amine | ethylen-imine | 400 | 10 | 2 | 84.2 | 69.3 | 58.4 |
| | | | | 3-amino-1-propanol | azetidine | 400 | 10 | 2 | 87.3 | 66.6 | 58.1 |
| 23 | Li = 0.1 Rb = 0.9 | 0.4 | Cu = 0.05 Nb = 20 | mono-ethanol-amine | ethylen-imine | 380 | 10 | 2 | 85.9 | 72.8 | 62.5 |
| | | | | 5-amino-1-pentanol | piperi-dine | 370 | 10 | 2 | 88.7 | 74.1 | 65.7 |
| 24 | K = 0.3 Mg = 0.7 | 1.0 | Ta = 3.0 Mo = 0.01 | mono-ethanol-amine | ethylen-imine | 360 | 10 | 2 | 79.4 | 67.3 | 53.4 |
| | | | | 2-amino-1-butanol | 2-ethyl-ethylen-imine | 360 | 10 | 2 | 81.0 | 68.0 | 55.1 |
| 25 | Ca = 1.0 | 0.7 | Zr = 30 W = 5 | mono-ethanol-amine | ethylen-imine | 410 420 | 10 | 2 300 | 69.7 67.9 | 83.1 84.2 | 57.9 57.2 |
| 26 | Cs = 0.7 Sr = 0.3 | 0.6 | Zr = 35 | mono-ethanol-amine | ethylen-imine | 400 | 20 | 2 | 62.9 | 86.2 | 54.2 |
| | | | | iso-propanol-amine | 2-methyl-ethylen-imine | 400 | 20 | 2 | 63.8 | 88.3 | 56.3 |
| 27 | Cs = 0.9 Ba = 0.1 | 0.6 | Ti = 0.1 Zr = 20 | mono-ethanol-amine | ethylen-imine | 400 420 | 10 | 2 500 | 75.7 73.3 | 88.9 90.1 | 67.3 66.0 |

TABLE 4

| Example | Catalyst composition (atomic ratio excepting oxygen) X | P | Y | Carrier (wt. %) | Starting alkanolamine (I) | Produced cyclic amine (II) | Reaction temperature (°C.) | Concentration of the starting alkanolamine (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|---|---|
| 28 | Na = 1 | 0.5 | — | Celite (85) | monoethanolamine | ethylenimine | 400 / 420 | 10 | 2 / 200 | 54.2 / 52.8 | 72.5 / 73.0 | 39.3 / 38.5 |
| 29 | Na = 1 | 0.5 | Sc = 0.1 | Zirconia (80) | monoethanolamine | ethylenimine | 410 / 420 | 10 | 2 / 200 | 75.8 / 75.1 | 82.0 / 82.4 | 62.2 / 61.9 |
| 30 | Rb = 1 | 0.3 | B = 0.01 | Silicagel (90) | monoethanolamine | ethylenimine | 410 | 10 | 2 | 73.3 | 79.6 | 58.3 |
|  |  |  | Ti = 0.02 |  | isopropanolamine | 2-methylethylenimine | 410 | 10 | 2 | 75.8 | 80.2 | 61.2 |
| 33 | Na = 0.3 | 0.6 | S = 0.03 | silica alumina (75) | monoethanolamine | ethylenimine | 420 | 10 | 2 | 76.1 | 80.3 | 61.1 |
|  | Mg = 0.7 |  | Cu = 0.01 |  | 3-amino-1-propanol | azetidine | 420 | 10 | 2 | 70.9 | 81.6 | 57.9 |
| 34 | Cs = 0.5 | 0.5 | Ta = 0.02 | zirconia (80) | monoethanolamine | ethylenimine | 420 / 430 | 20 | 2 / 200 | 63.9 / 62.0 | 81.0 / 82.0 | 51.8 / 50.8 |
|  | Ca = 0.5 |  | W = 0.04 |  |  |  |  |  |  |  |  |  |
| 35 | Na = 0.8 | 0.4 | Ce = 0.01 | silicon nitride (75) | monoethanolamine | ethylenimine | 390 | 10 | 2 | 75.5 | 78.1 | 59.0 |
|  | Mg = 0.2 |  | Zr = 0.08 |  | isopropanolamine | 2-methylethylenimine | 390 | 10 | 2 | 76.3 | 79.3 | 60.5 |
| 36 | Rb = 0.8 | 0.5 | Y = 0.02 | α-alumina (80) | monoethanolamine | ethylenimine | 400 / 415 | 10 | 2 / 200 | 82.1 / 81.3 | 83.4 / 84.0 | 68.5 / 68.3 |
|  | Ba = 0.2 |  | La = 0.05 |  |  |  |  |  |  |  |  |  |
| 37 | K = 0.1 | 0.6 | B = 0.05 | silicon carbide (75) | monoethanolamine | ethylenimine | 400 / 415 | 10 | 2 / 500 | 81.9 / 79.4 | 86.6 / 87.3 | 70.9 / 69.3 |
|  | Cs = 0.9 |  | Th = 0.01 |  |  |  |  |  |  |  |  |  |

TABLE 5

| Comparative Example | Catalyst composition (atomic ratio excepting oxygen) | Starting alkanolamine (I) | Produced cyclic amine (II) | SV (hr$^{-1}$) | Reaction temperature (°C.) | Concentration of the starting alkanolamine (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|
| 1 | $W_{1.0}Si_{0.5}$ | monoethanolamine | ethylenimine | 1,500 | 350 | 5 | 2 | 65.8 | 21.0 | 13.8 |
|  |  |  |  | 1,500 | 350 | 5 | 10 | 21.5 | 19.2 | 4.1 |
| 2 | $Nb_{1.0}Ba_{0.1}$ | monoethanolamine | ethylenimine | 1,500 | 420 | 5 | 2 | 45.1 | 69.2 | 31.2 |
|  |  |  |  | 1,500 | 420 | 5 | 10 | 18.2 | 74.3 | 13.5 |

What is claimed is:

1. A catalyst effective for the vapor phase intramolecular dehydration reaction of an alkanolamine to convert it into a cyclic amine wherein said catalyst is an oxide composition selected from the group consisting of $CaP_{0.5}O_d$, $SrP_{0.7}O_d$, $BaP_{0.7}O_d$, $Mg_{0.6}Ba_{0.4}P_{0.4}O_d$, $Ca_{0.9}Na_{0.1}P_{0.5}O_d$, $Ca_{0.9}Na_{0.1}P_{0.5}O_d$, $Sr_{0.6}Cs_{0.4}P_{0.1}O_d$, $LiP_{0.05}Si_{10}O_d$, $NaP_{0.5}Si_8B_{0.05}O_d$, $BaP_{0.2}S_{0.1}O_d$, $Mg_{0.3}Cs_{0.7}P_{0.7}Tl_{0.1}Al_{5.0}O_d$, $CaP_{0.5}Sn_{0.01}Sb_{0.01}O_d$, $BaP_{0.5}La_{0.05}Bi_{0.01}O_d$, $Rb_{0.2}Sr_{0.8}P_{0.3}Th_{0.02}Pb_{0.05}O_d$, $K_{0.4}Ca_{0.6}P_{0.6}Ce_{0.04}O_d$, $K_{0.4}Ca_{0.6}P_{0.6}Ce_{0.04}O_d$, $Ba_{0.5}Cs_{0.5}PSi_{50}O_d$, $NaP_{0.5}Sc_{0.1}Ti_7O_d$, $CsP_{0.7}Y_{0.1}Ti_{10}O_d$, $BaPMo_{0.01}O_d$, $K_{0.3}Mg_{0.7}PTa_{3.0}Mo_{0.01}O_d$, $Cs_{0.7}Sr_{0.3}P_{0.6}Zr_{35}O_d$, $Cs_{0.9}Ba_{0.1}P_{0.6}Ti_{0.1}Zr_{20}O_d$, $NaP_{0.5}O_d$, $NaP_{0.5}Sc_{0.1}O_d$, $RbP_{0.3}B_{0.01}Ti_{0.02}O_d$, $CsP_{0.7}Nb_{0.15}La_{0.02}O_d$, $K_{0.7}Ca_{0.3}P_{0.4}Si_{0.15}Al_{0.01}O_d$, $Na_{0.3}Mg_{0.7}P_{0.6}S_{0.03}Cu_{0.01}O_d$, $Cs_{0.5}Ca_{0.5}P_{0.5}Ta_{0.02}W_{0.04}O_d$, $Na_{0.8}Mg_{0.2}P_{0.4}Ce_{0.01}Zr_{0.08}O_d$, $Rb_{0.8}Ba_{0.2}P_{0.5}Y_{0.02}La_{0.05}O_d$, $Li_{0.1}Rb_{0.9}P_{0.4}Cu_{0.05}Nb_{20}O_d$, $CaP_{0.7}Zr_{30}W_5O_d$ and $K_{0.1}Cs_{0.9}P_{0.6}B_{0.05}Th_{0.01}O_d$, wherein "d" is a value determined by the state of bonding of the constituent elements in each respective oxide composition.

* * * * *